(12) United States Patent
Carroll et al.

(10) Patent No.: US 8,099,149 B2
(45) Date of Patent: Jan. 17, 2012

(54) MRI METHOD FOR QUANTIFICATION OF CEREBRAL PERFUSION

(75) Inventors: Timothy J. Carroll, Chicago, IL (US);
Wanyong Shin, Baltimore, MD (US);
Jessy J. Mouannes, Elmwood Park, IL (US)

(73) Assignee: Northwestern University, Evanston, IL (US)

( * ) Notice: Subject to any disclaimer, the term of this patent is extended or adjusted under 35 U.S.C. 154(b) by 1096 days.

(21) Appl. No.: 11/941,735

(22) Filed: Nov. 16, 2007

(65) Prior Publication Data
US 2008/0119720 A1     May 22, 2008

Related U.S. Application Data

(60) Provisional application No. 60/860,051, filed on Nov. 20, 2006.

(51) Int. Cl.
*A61B 5/055* (2006.01)
(52) U.S. Cl. ........................................ 600/419
(58) Field of Classification Search .............. 600/410, 600/419
See application file for complete search history.

(56) References Cited

U.S. PATENT DOCUMENTS
6,546,275 B2    4/2003    Carroll
2004/0044281 A1*    3/2004    Jesberger et al. ............. 600/419

OTHER PUBLICATIONS

W. Shin; T. J. Carroll; A Self Calibrating Pulse Sequence for Real Time Quantitative Cerebral Perfusion; Proc. Intl. Soc. Mag. Reson. Med. (2007).
Ken E. Sakaie; Wanyong Shin; Kenneth R. Curtin; Richard M. McCarthy; Ty A. Cashen; Timothy J. Carroll; Method for Improving the Accuracy of Quantitative Cerebral Perfusion Imaging; Journal of Magnetic Resonance Imaging 21:512-519 (2005).
Wanyong Shin; Ty A Cashen; Sandra W. Horowitz; Rahul Sawlani; Timothy J. Carroll; Quantitative CBV Measurement from Static T1 Changes in Tissue and Correction for Intravascular Water Exchange; Magnetic Resonance in Medicine 56:138-145 (2006); published online Jun. 9, 2006 at www.interscience.wiley.com.
Wangyon Shin, Sandra Horowitz, Ann Ragin, Yufen Chen, Matthew Walker, Timothy J. Carroll, Quantitative Cerebral Perfusion Using Dynamic Susceptibility Contrast MRI: Evaluation of Reproducibility and Age- and Gender-Dependence With Fully Automatic Image Postprocessing Algorithm, Mag. Reson. Med. 58:1232-1241 (2007).
A. Shaibani, S. Khawar, W. Shin, T. A. Cashen, B. Schirf, M. Rohany, S. Kakodkar, T. J. Carroll, First Results in an MR Imaging-Compatible Canine Model of Acute Stroke, Shaibani/AJNR 27/ Sep. 2006/ www.ajnr.org.

* cited by examiner

*Primary Examiner* — Jacquenline Cheng
(74) *Attorney, Agent, or Firm* — Quarles & Brady LLP

(57) ABSTRACT

A method for calculating quantitative perfusion measurements using an MRI system includes a pulse sequence that acquires perfusion weighted images and additionally measures $T_1$ values before and after the administration of a contrast agent. $T_1$ values are measured by rapidly sampling a longitudinal relaxation curve and employed to determine the blood volume in tissue. A correction factor for the effect of water diffusion between blood vessels and the extravascular space is determined.

24 Claims, 5 Drawing Sheets

MRI METHOD FOR QUANTIFICATION OF CEREBRAL PERFUSION

CROSS-REFERENCE TO RELATED APPLICATIONS

This application claims the benefit of U.S. Provisional patent application Ser. No. 60/860,051 filed on Nov. 20, 2006 and entitled "MRI Method For Quantification Of Cerebral Perfusion".

STATEMENT REGARDING FEDERALLY SPONSORED RESEARCH

This invention was made with United States government support awarded by the following agency: NIH grants: R01 NS049395-01A2. The United States has certain rights in this invention.

BACKGROUND OF THE INVENTION

The field of the invention is nuclear magnetic resonance imaging methods and systems. More particularly, the invention relates to the quantitative measurement of cerebral perfusion with an MRI system.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Perfusion as related to tissue refers to the exchange of oxygen, water and nutrients between blood and tissue. The measurement of tissue perfusion is important for the functional assessment of organ health. Perfusion weighted images (PWI) show the degree to which tissues are perfused by the change in their brightness as a bolus of contrast agent washes through the vasculature, and can be used to assess the health of brain tissues that have been damaged by a stroke. A number of methods have been used to produce perfusion images using magnetic resonance imaging techniques. One technique, as exemplified by U.S. Pat. No. 6,295,465, is to determine the wash-in or wash-out kinetics of contrast agents such as chelated gadolinium. From the acquired NMR data, images are produced which indicate cerebral blood flow (CBF), cerebral blood volume (CBV), and mean transit time (MTT) at each voxel. Each of these perfusion indication measurements provides information that is useful in diagnosing tissue health.

Bolus tracking cerebral perfusion has expansive use in the clinical setting for imaging a variety of diseases including cerebrovascular occlusive disease, stroke, central nervous system tumors, and Alzheimer's disease. Parametric images of cerebral perfusion are calculated by analyzing the tracer kinetics of a known contrast agent, whether it is radio-labeled water in positron emission tomography (PET), an iodinated contrast agent in computed tomography (CT), spin-labeled water in arterial spin labeling MRI, or a paramagnetic contrast agent in dynamic susceptibility contrast (DSC) MRI. While the standard for quantification of cerebral perfusion still remains radio-labeled PET imaging, the requirement of a cyclotron for production of the radio-labeled tracer limits the availability of the technique. CT has the potential to quantify perfusion; however, iodinated contrast agents and large doses of radiation are required in this imaging method. This is problematic for frequent follow-up scan session as well as the use of the method in certain patient populations, such as young children.

MR-based perfusion imaging methods produce parametric images that only convey information relating to relative, and not quantitative, cerebral blood flow (rCBF) and cerebral blood volume (rCBV). Current methods for creating quantitative measurements of perfusion from MR imaging data rely on assuming population averaged values of normal appearing white matter (WM) and by setting the CBF values in this tissue to a preset value. This method has a poor correlation to PET imaging standards. Instead, a method which determines the quantitative CBF and CBV (qCBF and qCBV, respectively) on a subject-by-subject basis would be preferred.

SUMMARY OF THE INVENTION

The present invention overcomes the aforementioned drawbacks by providing a method for the determination of quantitative perfusion measurements using an MRI system. More particularly, an imaging pulse sequence is performed to acquire perfusion weighted image data between the rapid acquisition of $T_1$-weighted images acquired before and after the injection of a $T_1$-shortening contrast agent that is used to assess relative changes in tissue perfusion. Quantitative perfusion images are then produced by utilizing the information acquired during the above-mentioned pulse sequence.

The present invention is an automated method for determining quantitative perfusion measurements using an MRI system that employs a correction factor for the effects of water diffusion across the walls of the vasculature. Thus, accurate measurements of quantitative perfusion can be achieved without the exposure to large doses of radiation, such as in CT perfusion imaging, or without the administration of a radio-labeled tracer agent, such as in PET imaging. The method will allow quantitative perfusion imaging to reach a broader clinical population.

DETAILED DESCRIPTION OF THE PREFERRED EMBODIMENT

Figure 1:
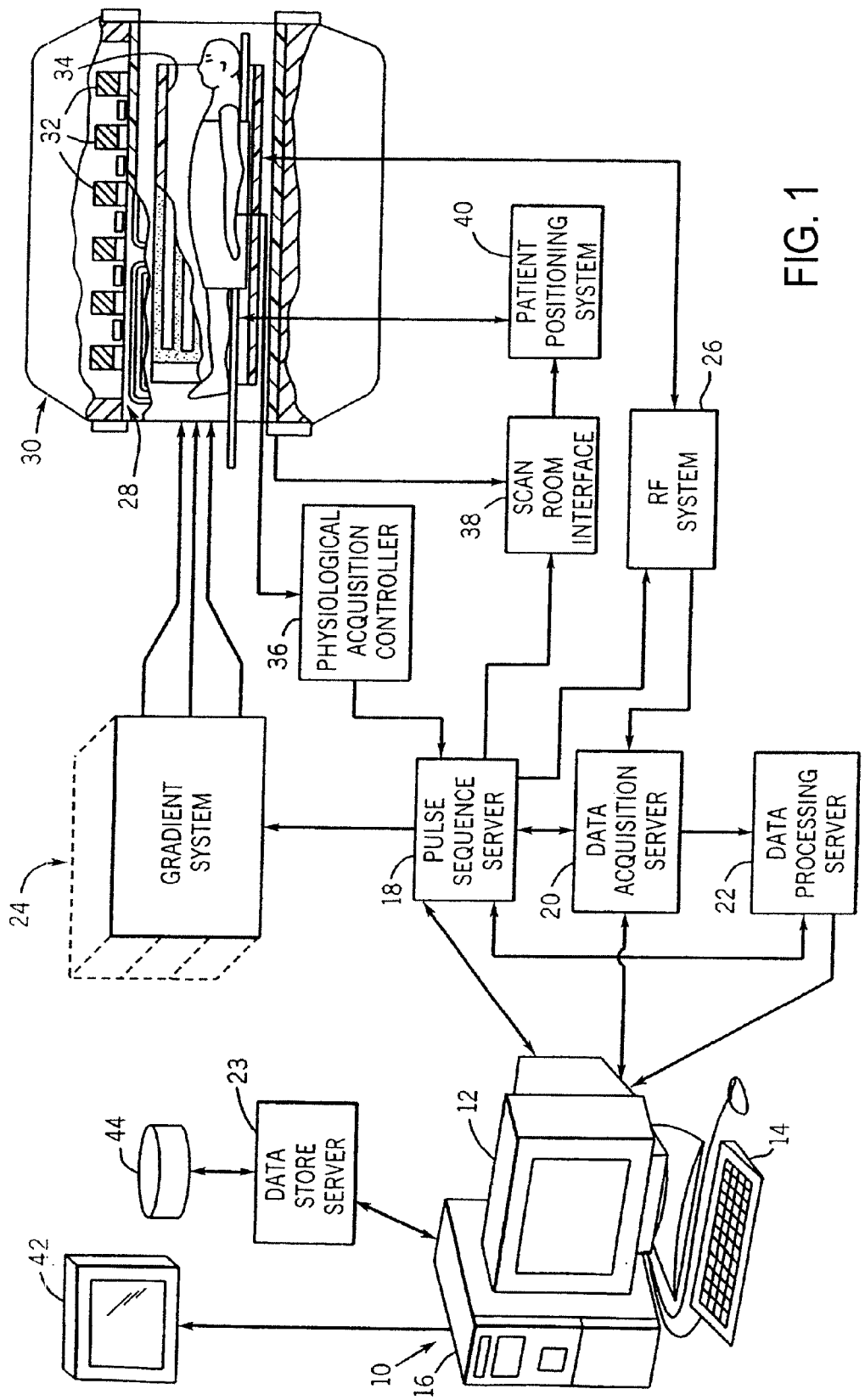
FIG. 1 is a block diagram of an MRI system which employs the present invention.

Referring particularly to FIG. 1, the preferred embodiment of the invention is employed in an MRI system. The MRI system includes a workstation 10 having a display 12 and a keyboard 14. The workstation 10 includes a processor 16 which is a commercially available programmable machine running a commercially available operating system. The workstation 10 provides the operator interface which enables scan prescriptions to be entered into the MRI system.

The workstation 10 is coupled to four servers: a pulse sequence server 18; a data acquisition server 20; a data processing server 22, and a data store server 23. In the preferred embodiment the data store server 23 is performed by the workstation processor 16 and associated disc drive interface circuitry. The server 18 is performed by a separate processor and the servers 20 and 22 are combined in a single processor. The workstation 10 and each processor for the servers 18, 20 and 22 are connected to an Ethernet communications network. This network conveys data that is downloaded to the servers 18, 20 and 22 from the workstation 10, and it conveys data that is communicated between the servers.

The pulse sequence server 18 functions in response to instructions downloaded from the workstation 10 to operate a gradient system 24 and an RF system 26. Gradient waveforms necessary to perform the prescribed scan are produced and applied to the gradient system 24 which excites gradient coils in an assembly 28 to produce the magnetic field gradients Gx, Gy and Gz used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 18. The RF system 26 includes an RF transmitter for producing a wide variety of RF pulses used in MR pulse sequences. The RF transmitter is responsive to the scan prescription and direction from the pulse sequence server 18 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2+Q^2},$$

and the phase of the received NMR signal may also be determined:

$$\phi=\tan^{-1}Q/I.$$

The pulse sequence server 18 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 18 to synchronize, or "gate", the performance of the scan with the subject's respiration or heart beat.

The pulse sequence server 18 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

The digitized NMR signal samples produced by the RF system 26 are received by the data acquisition server 20. The data acquisition server 20 operates in response to instructions downloaded from the workstation 10 to receive the real-time NMR data and provide buffer storage such that no data is lost by data overrun. In some scans the data acquisition server 20 does little more than pass the acquired NMR data to the data processor server 22. However, in scans which require information derived from acquired NMR data to control the further performance of the scan, the data acquisition server 20 is programmed to produce such information and convey it to the pulse sequence server 18. For example, during prescans NMR data is acquired and used to calibrate the pulse sequence performed by the pulse sequence server 18. Also, navigator signals may be acquired during a scan and used to adjust RF or gradient system operating parameters or to control the view order in which k-space is sampled. And, the data acquisition server 20 may be employed to process NMR signals used to detect the arrival of contrast agent in an MRA scan. In all these examples the data acquisition server 20 acquires NMR data and processes it in real-time to produce information which is used to control the scan.

The data processing server 22 receives NMR data from the data acquisition server 20 and processes it in accordance with instructions downloaded from the workstation 10. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 22 are conveyed back to the workstation 10 where they are stored. Real-time images are stored in a data base memory cache (not shown) from which they may be output to operator display 12 or a display 42 which is located near the magnet assembly 30 for use by attending physicians. Batch mode images or selected real time images are stored in a host database on disc storage 44. When such images have been reconstructed and transferred to storage, the data processing server 22 notifies the data store server 23 on the workstation 10. The workstation 10 may be used by an operator to archive the images, produce films, or send the images via a network to other facilities.

The key problem in the derivation of quantitative perfusion values is that of defining an appropriate scale factor that can convert the values of flow into physiologically meaningful perfusion (in ml of blood/gram of tissue/minute). Perfusion is normally reported as ml/100 g-minute. To determine this scale factor we have derived a MRI pulse sequence that uses a self-calibration technique. This requires a very rapid measurement of the longitudinal relaxation time, $T_1$, of the brain tissue to be performed.

Figure 2:
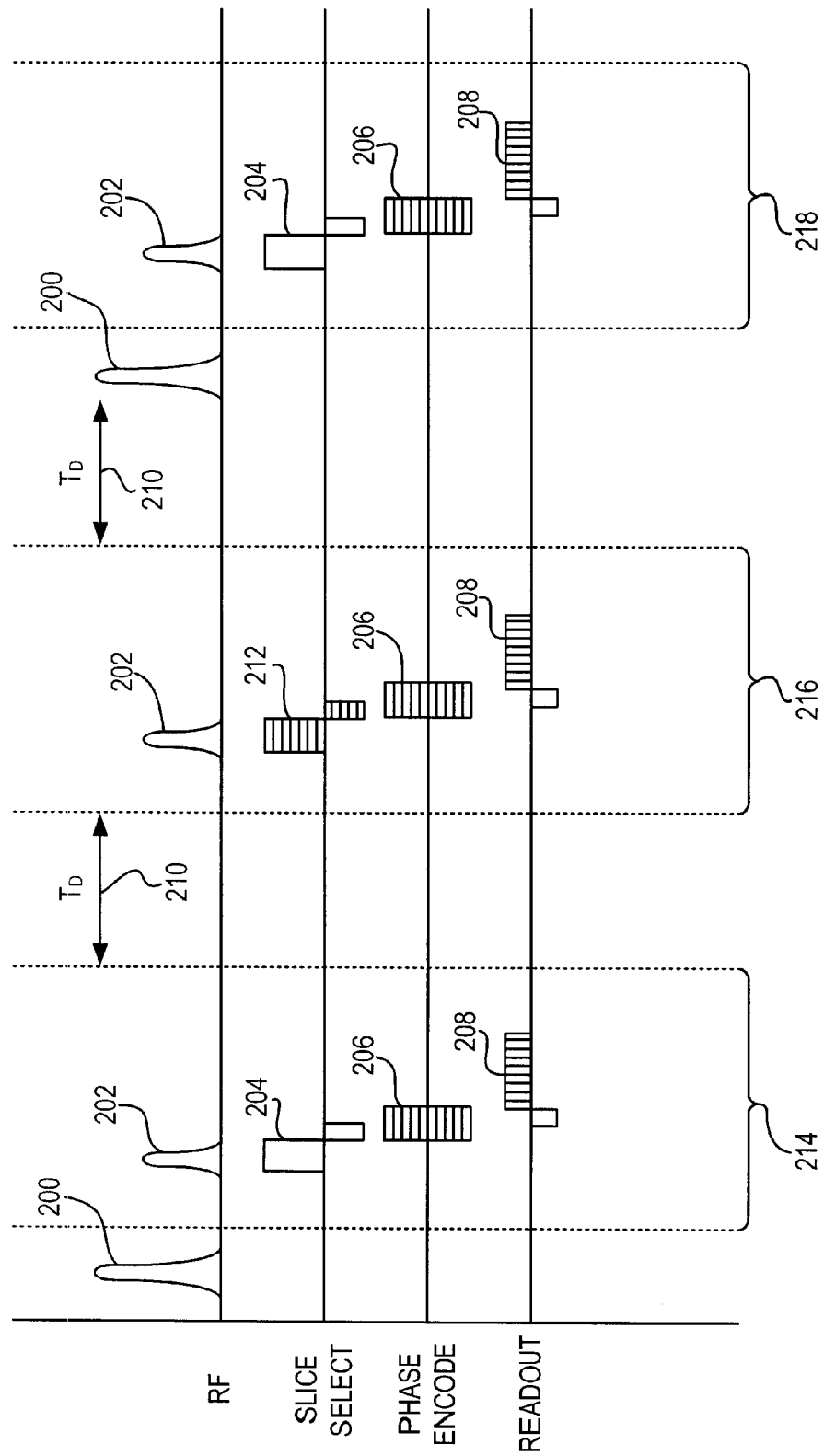
FIG. 2 is a graphic illustration of a preferred pulse sequence employed by the MRI system of FIG. 1 to practice the present invention.
Figure 4:
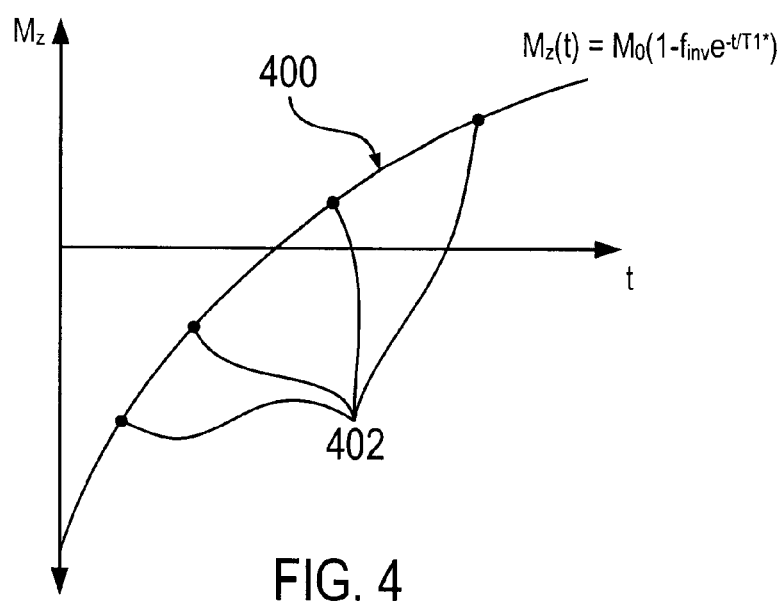
FIG. 4 is a graphical illustration of a magnetization regrowth curve measured by the pulse sequence of FIG. 2

As shown in FIG. 2, a non-slice-selective inversion recovery (IR) pulse 200 precedes a look-locker echo-planar image (LL-EPI) acquisition 214. The LL-EPI sequence includes a 20 degree RF excitation pulse 202, a slice select gradient lobe 204 that excites at least one slice from which NMR signals are acquired, a phase encoding gradient lobe 206, and a rapid readout gradient 208. The combination of the IR pulse with the LL-EPI sequence allows for the rapid measurement of the $T_1$ relaxation curve 400, which is shown in FIG. 4. This method allows for accurate measurements of $T_1$ by effectively sampling the relaxation curve 400 at multiple points 402, after which a regression method such as a least squares procedure is performed to estimate $T_1$. After the LL-EPI sequence 214 is performed, a contrast agent is injected into the subject and a standard perfusion weighted imaging sequence 216 is employed to acquire NMR imaging data from which relative perfusion parametric maps will be produced. The preferred perfusion weighted imaging sequence 216 is a gradient echo EPI (GRE-EPI) pulse sequence; however, in an alternative embodiment a spin echo EPI pulse sequence is employed. The GRE-EPI sequence includes a 90 degree RF excitation pulse 202, a slice select gradient lobe 212 that excites multiple slices in the imaging volume, a phase encoding gradient lobe 206, and a rapid readout gradient 208. A second, post contrast, LL-EPI sequence 218 is performed after the acquisition of the perfusion weighted images and is preceded by another IR pulse 200. In one embodiment, a nominal delay time 210, $T_D$, is added before and after the perfusion weighted acquisition 216 to allow full recovery of the magnetization between excitations of the imaging volume.

Figure 3:
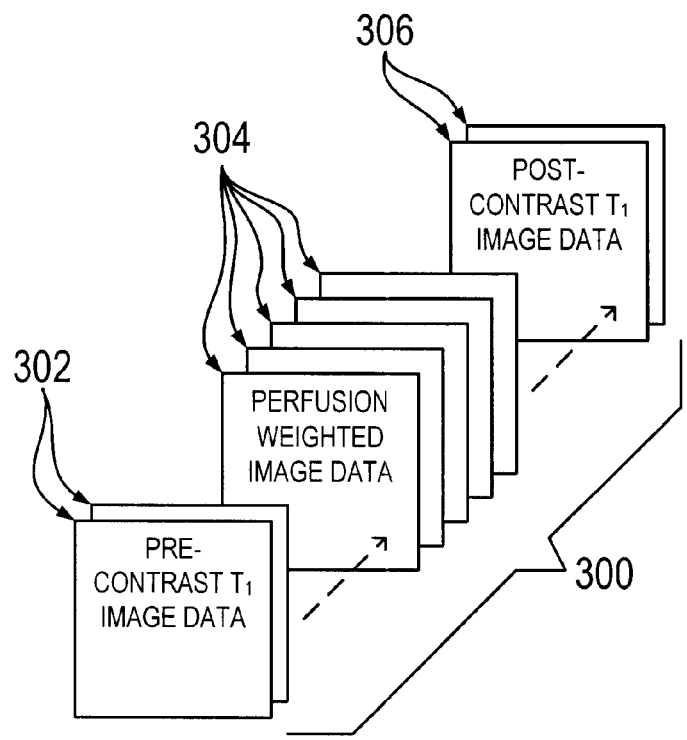
FIG. 3 is a pictorial view of the image data sets acquired by the MRI system of FIG. 1 after performing the pulse sequence of FIG. 2.
Figure 5:
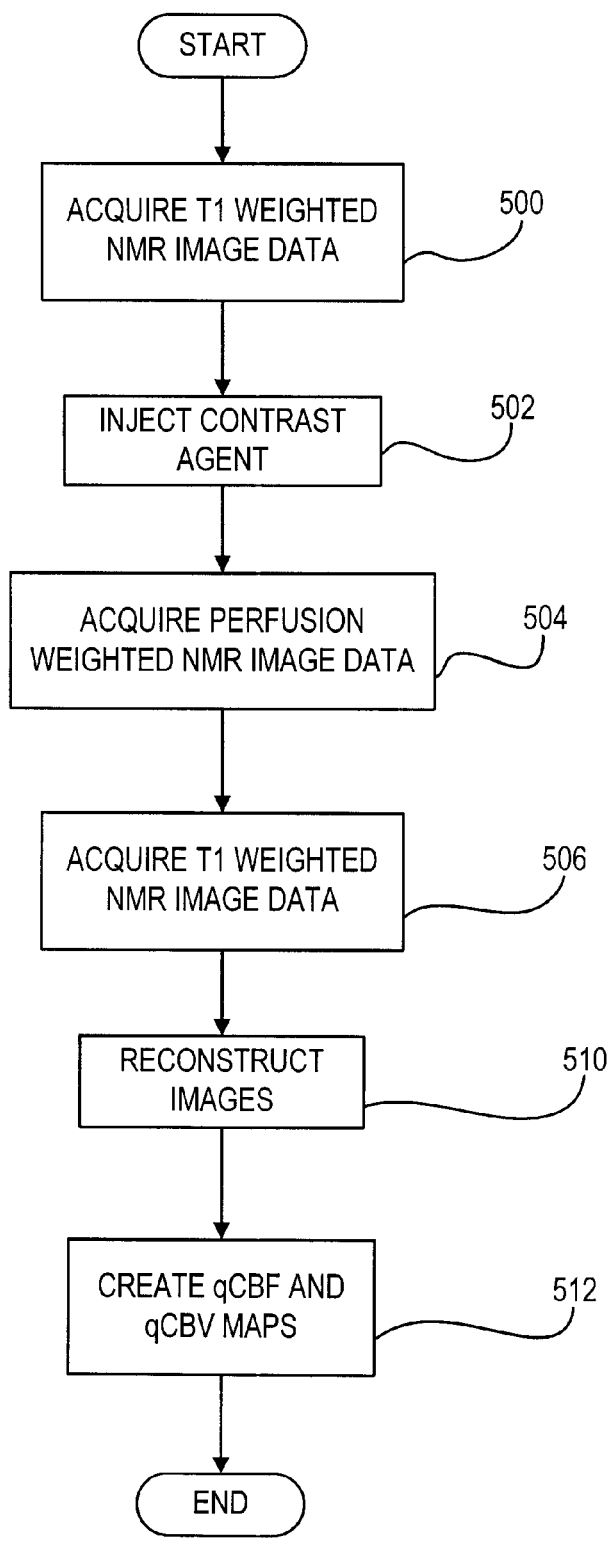
FIG. 5 is a flowchart of the image data acquisition process carried out by the pulse sequence of FIG. 2.

The general process for the production of quantitative perfusion parametric maps is shown in FIG. 5. First, the pre-contrast LL-EPI 214 segment of the pulse sequence of FIG. 2 is employed to acquire $T_1$ measurements prior to the administration of a contrast agent, as shown in process block 500. Next, a contrast agent is administered to the subject in step 502 and the perfusion weighted NMR data is acquired in step 504. Then, post-contrast $T_1$ image data are acquired in process block 506 by employing the second LL-EPI segment 218 of the pulse sequence of FIG. 2. The corresponding $T_1$ and perfusion weighted images are reconstructed in step 510 before the producing the quantitative perfusion parametric maps in step 512. A representative image data set 300 is shown in FIG. 3. At least one image slice is acquired for the pre-contrast $T_1$ imaging data 302 and for the post-contrast $T_1$ imaging data 306. Additionally, a set of multiple image slices are acquired for the perfusion weighted imaging data 304 in order to cover the 3D volume of interest.

Figure 6:
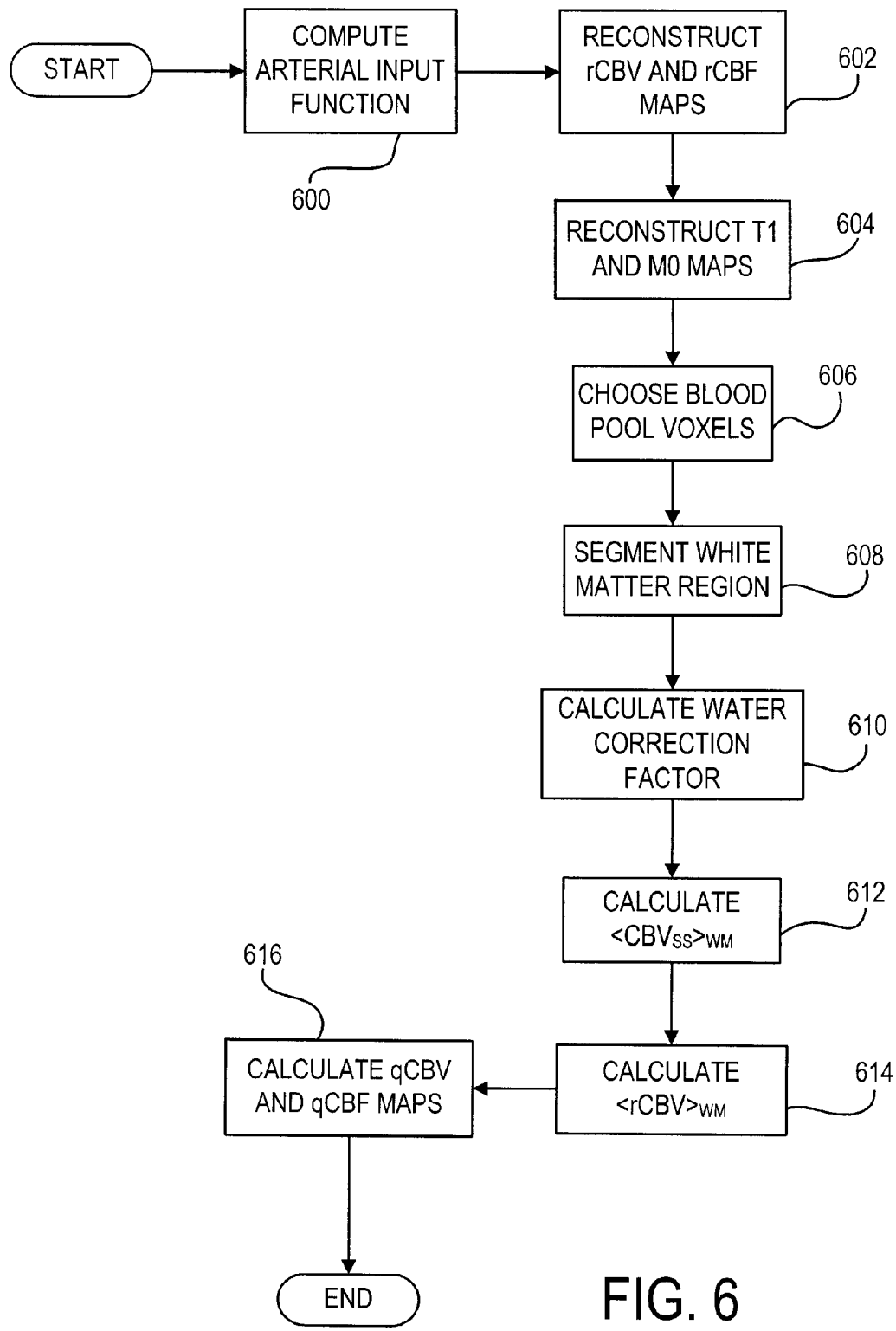
FIG. 6. is a flowchart of the post imaging processing method for determining the quantitative perfusion parameters.

Referring particularly to FIG. 6, a method for producing quantitative perfusion parametric maps is presented. First, maps of the relative cerebral blood flow and cerebral blood volume (rCBF and rCBV, respectively) are produced. This process involves the computation of an arterial input function (AIF) in step 600. The preferred method for producing an AIF is similar to the automatic method disclosed in U.S. Pat. No. 6,546,275 which is incorporated herein by reference. Next, rCBF and rCBV maps are reconstructed in step 602 using the calculated AIF and the perfusion weighted images reconstructed from the perfusion weighted image data 304. A known technique such as that disclosed in U.S. Pat. No. 6,546,275 is used to produce these relative value maps, rCBF and rCBV. An alternative method of calculating rCBF is to perform a mathematical deconvolution of each voxel's concentration versus time curve using the AIF as has been described by L. Ostergaard et al "High Resolution Measurements of Cerebral Blood Flow Using Intravascular Tracer Bolus Passages. Part 1: Mathematical Approach and Statistical Analysis", Magnetic Resonance in Medicine, 36:715-725 (1996).

Using the images reconstructed from the acquired pre- and post-contrast $T_1$ imaging data, measurement maps of both the pre- and post-contrast $T_1$ and $M_0$ are created in step 504. This is achieved by fitting the signal recovery curves of each voxel in the images to a monoexponential described by:

$$M(t)=M_0(1-f_{inv}e^{-t/T^*_1})$$

where $M_0$ is the initial magnetization, $f_{inv}$ is an inversion factor (when the delay between inversion pulses is sufficient to allow complete longitudinal recovery of the magnetization, $f_{inv}$ is equal to 2), and $T_1^*$ is the apparent $T_1$ of the voxel. The true $T_1$ of the voxel is then determined by:

$$T_1 = T^*_1(f_{inv}-1)$$

Next, at least one voxel containing substantially only blood, referred to as a blood pool voxel, is automatically located in step 506. In the preferred embodiment, the blood pool voxel is located in the sagittal sinus; however, other vasculature can be selected. The blood pool voxel is determined by evaluating the longitudinal relaxation rates in the pre- and post-contrast $T_1$ measurement maps, which can be calculated by the following relationship:

$$R_1 = \frac{1}{T_1},$$

where $R_1$ is the longitudinal relaxation rate and $T_1$ is the measured longitudinal relaxation time. The blood pool voxel is thus determined by finding a voxel that has a substantially large $R_1$ rate of change between the post- and pre-contrast $T_1$ measurement maps relative to other voxels in the maps. The $R_1$ rate of change, $dR_1$, is calculated by:

$$dR_1 = (R_1^{post} - R_1^{pre}),$$

where $R_1^{post}$ is the longitudinal relaxation rate of a voxel determined from the post-contrast $T_1$ measurement map and $R_1^{pre}$ is the longitudinal relaxation rate of a voxel determined from the pre-contrast $T_1$ measurement map.

An automatic white matter selection process is performed in step 508. From the reconstructed pre- and post-contrast $T_1$ measurement maps a $T_1$ distribution is produced. Only the voxels that have a value within the full-width half-maximum of the largest peak of the $T_1$ distribution will be included in the segmented white matter map. Using the reconstructed $T_1$ measurement maps, a correction factor for the effects of water exchange in the vasculature is calculated in step 510. The water correction factor is determined by:

$$WCF_{1.5T}=8.2\times10^{-3}dR_{1,blood}^2+0.25dR_{1,blood}+0.51$$

$$WCF_{3T}=9.5\times10^{-3}dR_{1,blood}^2+0.30dR_{1,blood}+0.52$$

where $WCF_{1.5T}$ is the water correction factor at 1.5 T, $WCF_{3T}$ is the water correction factor at 3.0 T, and $dR_{1,blood}$ is the rate of change of the longitudinal relaxation rate in the blood pool voxel.

Next, an average value of steady state cerebral blood volume in the segmented white matter region ($CBV_{SS,WM}$) is calculated in step 512. In the context of the present invention "steady state" refers to the distribution phase of the MRI contrast agent within the blood pool. First, $CBV_{SS,WM}$ is determined for each voxel in the segmented white matter region by:

$$CBV_{SS,WM} = \frac{K_H}{\rho} \times \left( \frac{R_{1,tissue}^{post} - R_{1,tissue}^{pre}}{R_{1,blood}^{post} - R_{1,blood}^{pre}} \right)$$

where $\rho$ is the average density in brain tissue (1.04 g/100 mL), $K_H$ is a hematocrit correction factor, which compensates for the difference in densities between brain tissue and blood, having a value of 0.71, $R_{1,tissue}^{post}$ is the longitudinal relaxation rate of the tissue determined from the reconstructed post-contrast $T_1$ measurement map, $R_{1,tissue}^{pre}$ is the longitudinal relaxation rate of the tissue determined from the reconstructed pre-contrast T, measurement map, $R_{1,blood}^{post}$ is the longitudinal relaxation rate of the selected blood pool determined from the reconstructed post-contrast $T_1$ measurement map, and $R_{1,blood}^{pre}$ is the longitudinal relaxation rate of the selected blood pool determined from the reconstructed post-contrast $T_1$ measurement map. From this calculation a distribution of the $CBV_{SS,WM}$ is determined. In an alternative embodiment, the $CBV_{SS,WM}$ values can be calculated using the signal intensity values of voxels in both the tissue and the blood pool in a pre- and post-contrast $T_1$-weighted image instead of the $R_1$ values of the tissue and blood pool as described above. A measurement of the average $CBV_{SS,WM}$ can then be determined by fitting the $CBV_{SS,WM}$ distribution to a Gaussian distribution having the form:

$$Y = A \cdot e^{-\left(\frac{CBV_{SS,WM} - \langle CBV_{SS,WM}\rangle}{\sqrt{2\sigma}}\right)^2}$$

where Y is the distribution of $CBV_{SS,WM}$, A is a constant, $\langle CBV_{SS,WM}\rangle$ is the average steady state cerebral blood volume in the white matter region, and $\sigma$ is the standard deviation of the steady state cerebral blood volume in the white matter region.

An average value of rCBV in the segmented white matter region of step 508, $\langle rCBV_{WM}\rangle$, is calculated in step 514. Finally, the quantitative CBF and CBV maps (qCBF and qCBV, respectively) are produced in step 516. The method of computing qCBV is as follows:

$$qCBV = WCF \times \frac{\langle CBV_{SS,WM}\rangle}{\langle rCBV_{WM}\rangle} \times rCBV,$$

where WCF is the water correction factor calculated in step 510, rCBV is the relative CBV value calculated in step 502, $\langle CBV_{SS,WM}\rangle$ is the average steady state cerebral blood volume in the white matter region, and $\langle rCBV\rangle_{WM}$ is the average rCBV value in the segmented white matter region of step 508, which is calculated in step 514. The method for computing qCBF is given by:

$$qCBF = WCF \times \frac{\langle CBV_{SS,WM}\rangle}{\langle rCBV_{WM}\rangle} \times rCBF$$

where WCF is the water correction factor calculated in step 510, rCBF is the relative CBF value calculated in step 502, $\langle CBV_{SS,WM}\rangle$ is the average steady state cerebral blood volume in the white matter region, and $\langle rCBV\rangle_{WM}$ is the average rCBV in the segmented white matter region of step 508, which is calculated in step 514 as described above.

The method described above yields quantitative measurements of cerebral perfusion from imaging data acquired using an MRI system. Where previous quantitative measurements of cerebral perfusion were practically restricted to PET and CT imaging systems that expose the subject to be imaged to large doses of radiation, the present method uses no such radiation. Therefore, quantitative measurements of perfusion can be acquired through noninvasive means in a wider population. This is especially remarkable since the clinical uses of quantitative information relating to the perfusion process have substantial impact in numerous clinical diagnoses.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing a quantitative perfusion image of a subject using a magnetic resonance imaging (MRI) system, the steps comprising:
    a) acquiring pre-contrast $T_1$ image data with the MRI system;
    b) administering a contrast agent to the subject;
    c) acquiring perfusion weighted image data with the MRI system;
    d) acquiring post-contrast $T_1$ image data with the MRI system;
    e) calculating relative perfusion images using the perfusion weighted image data acquired in step c);
    f) calculating a quantitative perfusion image using the images calculated in step e) and the $T_1$ image data acquired in steps a) and d).

2. The method as recited in claim 1 wherein a preset delay time ($T_D$) is imposed between steps a) and c) and between steps c) and d).

3. The method as recited in claim 1 wherein step f) further comprises:
    f)i) reconstructing a pre-contrast $T_1$ measurement map from the pre-contrast $T_1$ image data acquired in step a); and
    f)ii) reconstructing a post-contrast $T_1$ measurement map from the post-contrast $T_1$ image data acquired in step d).

4. The method as recited in claim 3 wherein step f) further comprises:
    f)iii) determining at least one blood pool voxel from the pre-contrast and post-contrast $T_1$ image data acquired in acquired in steps a) and d); and
    f)iv) calculating a water correction factor from the pre-contrast and post-contrast $T_1$ image data acquired in acquired in steps a) and d).

5. The method as recited in claim 4 wherein step f) further comprises:
    f)v) identifying a region of tissue from the $T_1$ image data acquired in steps a) and d) to select voxels including a desired tissue.

6. The method as recited in claim 5 wherein step f) further comprises:
    f)vi) calculating an average steady state blood volume value in the region of tissue identified in step f)v); and
    f)vii) calculating an average relative blood volume in the region of tissue identified in step f)v).

7. The method as recited in claim 6 wherein step f)vii) further comprises averaging the value of each voxel in the relative blood volume image identified in the region of tissue identified in step f)v).

8. The method as recited in claim 6 wherein step f)vi) further comprises
    calculating a steady state blood volume value for each voxel in the region of tissue identified in step f)v); and
    fitting the calculated values of the steady state blood volume to a model.

9. The method as recited in claim 8 wherein the calculated steady state blood volume is calculated according to:

$$CBV_{SS,WM} = \frac{K_H}{\rho} \times \left( \frac{R_{1,tissue}^{post} - R_{1,tissue}^{pre}}{R_{1,blood}^{post} - R_{1,blood}^{pre}} \right)$$

wherein $\rho$ is an average tissue density for the region of tissue identified in step f)v);

wherein $K_H$ is a hematocrit correction factor;

wherein $R_{1,tissue}^{post}$ is a longitudinal relaxation rate for a voxel determined from the reconstructed post-contrast $T_1$ measurement map in the region of tissue identified in step f)v);

wherein $R_{1,tissue}^{pre}$ is a longitudinal relaxation rate for a voxel determined from the reconstructed pre-contrast $T_1$ measurement map in the region of tissue identified in step f)v);

wherein $R_{1,blood}^{post}$ is a longitudinal relaxation rate for the at least one blood pool voxel determined in step f)iii) in the reconstructed post-contrast $T_1$ measurement map; and wherein $R_{1,blood}^{pre}$ is a longitudinal relaxation rate for the at least one blood pool voxel determined in step f)iii) in the reconstructed pre-contrast $T_1$ measurement map.

10. The method as recited in claim 8 wherein the model is a Gaussian distribution.

11. The method as recited in claim 8 wherein the calculated steady state blood volume for each voxel in step f)vi) is determined using $T_1$ measurements from the reconstructed pre-contrast and reconstructed post-contrast $T_1$ measurement maps.

12. The method as recited in claim 8 wherein the calculated steady state blood volume for each voxel in step f)vi) is determined using signal values from the acquired pre-contrast and acquired post-contrast $T_1$ image data.

13. The method as recited in claim 6 wherein the quantitative perfusion image calculated in step f) is a quantitative cerebral blood flow image and has voxel values calculated according to:

$$qCBF = WCF \times \frac{\langle CBV_{SS,WM} \rangle}{\langle rCBV_{WM} \rangle} \times rCBF;$$

wherein WCF is the water correction factor calculated in step f)iv);

wherein $\langle CBV_{SS,WM} \rangle$ is the average steady state blood volume in the region of tissue identified in step f)v), as calculated in step f)vi);

wherein $\langle rCBV_{WM} \rangle$ is the average relative blood volume in the region of tissue identified in step f)v), as calculated in step f)vii); and wherein rCBF is a relative cerebral blood flow in a voxel calculated in step e).

14. The method as recited in claim 6 wherein the quantitative perfusion image calculated in step f) is a quantitative cerebral blood volume image and has voxel values calculated according to:

$$qCBV = WCF \times \frac{\langle CBV_{SS,WM} \rangle}{\langle rCBV_{WM} \rangle} \times rCBV;$$

wherein WCF is the water correction factor calculated in step f)iv);

wherein $\langle CBV_{SS,WM} \rangle$ is the average steady state blood volume in the region of tissue identified in step f)v), as calculated in step f)vi);

wherein $\langle rCBV_{WM} \rangle$ is the average relative blood volume in the region of tissue identified in step f)v), as calculated in step f)vii); and wherein rCBV is a relative cerebral blood volume in a voxel calculated in step e).

15. The method as recited in claim 5 wherein the subject is a brain and the desired tissue in the region of tissue identified in step f)v) is white matter.

16. The method as recited in claim 5 wherein step f)v) further comprises selecting voxels in the reconstructed pre-contrast $T_1$ measurement map having values within a desired range.

17. The method as recited in claim 16 wherein the desired range is identified by determining a full-width at half-maximum of a distribution of voxel values in the reconstructed pre-contrast $T_1$ measurement map.

18. The method as recited in claim 4 wherein step f)iii) further comprises:
    selecting at least one voxel having substantially larger values in the pre-contrast $T_1$ measurement map reconstructed in step f)i) than in the post-contrast $T_1$ measurement map reconstructed in step f)ii).

19. The method as recited in claim 4 wherein step f)iv) further comprises:
    calculating a difference between a longitudinal relaxation rate for at least one voxel in the reconstructed post-contrast $T_1$ measurement map and a longitudinal relaxation rate for at least one voxel in the reconstructed pre-contrast $T_1$ measurement map; and
    fitting the difference to a model.

20. The method as recited in claim 19 wherein the at least one voxel is the at least one blood pool voxel determined in step f)iii).

21. The method as recited in claim 19 wherein the model is a second order polynomial function.

22. The method as recited in claim 1 wherein the $T_1$ image data acquired in steps a) and d) is acquired using an inversion recovery pulse sequence.

23. The method as recited in claim 22 wherein the inversion recovery pulse sequence is an inversion recovery look-locker echo planar imaging pulse sequence.

24. The method as recited in claim 1 wherein the perfusion weighted image data acquired in step c) is acquired using an echo planar imaging pulse sequence.

* * * * *

UNITED STATES PATENT AND TRADEMARK OFFICE
CERTIFICATE OF CORRECTION

PATENT NO.       : 8,099,149 B2
APPLICATION NO.  : 11/941735
DATED            : January 17, 2012
INVENTOR(S)      : Timothy J. Carroll, Wanyong Shin and Jessy J. Mouannes It is certified that error appears in the above-identified patent and that said Letters Patent is hereby corrected as shown below:

Column 1, lines 15-18 should be replaced with the following: --This invention was made with government support under R01 NS049395-01-A2 awarded by National Institutes of Health. The government has certain rights in the invention.--

Signed and Sealed this
Thirteenth Day of March, 2012

David J. Kappos
*Director of the United States Patent and Trademark Office*